US012560589B2

(12) United States Patent
Ebbesen et al.

(10) Patent No.: US 12,560,589 B2
(45) Date of Patent: Feb. 24, 2026

(54) BLOOD GAS ANALYZER AND SYSTEM COMPRISING A BLOOD GAS ANALYZER, AND USE THEREOF

(71) Applicant: RADIOMETER MEDICAL APS, Brønshøj (DK)

(72) Inventors: Thea Ubbe Ebbesen, Brønshøj (DK); Ida Kjaergaard Baumgarten, Brønshøj (DK)

(73) Assignee: RADIOMETER MEDICAL APS, Brønshøj (DK)

( * ) Notice: Subject to any disclaimer, the term of this patent is extended or adjusted under 35 U.S.C. 154(b) by 559 days.

(21) Appl. No.: 18/004,462

(22) PCT Filed: Jul. 9, 2021

(86) PCT No.: PCT/EP2021/069142
§ 371 (c)(1),
(2) Date: Jan. 6, 2023

(87) PCT Pub. No.: WO2022/008714
PCT Pub. Date: Jan. 13, 2022

(65) Prior Publication Data
US 2024/0241106 A1     Jul. 18, 2024

(30) Foreign Application Priority Data

Jul. 10, 2020     (EP) .................................... 20185272

(51) Int. Cl.
*G01N 33/49*         (2006.01)
*G01N 35/00*         (2006.01)
*G01N 35/10*         (2006.01)

(52) U.S. Cl.
CPC ...  *G01N 33/4925* (2013.01); *G01N 35/00722* (2013.01); *G01N 35/1011* (2013.01);
(Continued)

(58) Field of Classification Search
None
See application file for complete search history.

(56) References Cited

U.S. PATENT DOCUMENTS

2009/0069639 A1 *  3/2009  Linssen .................. G01N 15/12
                                                      600/300
2009/0078717 A1 *  3/2009  Kowari .............. G01N 35/1011
                                                      422/68.1
(Continued)

FOREIGN PATENT DOCUMENTS

JP        2016/537627  A     12/2016
WO        2017/108646  A1     6/2017
(Continued)

OTHER PUBLICATIONS

International Search Report of International Application No. PCT/EP2021/069142, dated Sep. 27, 2021 (two pages).
(Continued)

*Primary Examiner* — Brian R Gordon
(74) *Attorney, Agent, or Firm* — FBT Gibbons LLP

(57)             ABSTRACT
A blood gas analyzer for performing a measurement of analytes in a blood sample, such as a whole blood sample, aspirated into the blood gas analyzer from a handheld blood sample container includes a controller, and a sensor system for detecting a presence, a position and/or an orientation of the handheld blood sample container relative to an inlet structure. An aspiration system is provided for aspirating the blood sample from the handheld blood sample container, the aspiration system connectable to the handheld blood sample container. A user interface system is provided for outputting instructions to a user of the blood gas analyzer, the instructions being selected among pre-stored sets of instructions. The controller selects one of the at least two pre-stored sets of instructions based on an assessment of a signal retrieved from the sensor system.

15 Claims, 6 Drawing Sheets

(52) U.S. Cl.
CPC .............. *G01N 2035/00891* (2013.01); *G01N 2035/1013* (2013.01)

(56) References Cited

U.S. PATENT DOCUMENTS

| | | | | |
|---|---|---|---|---|
| 2009/0244068 A1* | 10/2009 | Ikeda | ............... | G01N 35/00732 382/134 |
| 2010/0080440 A1* | 4/2010 | Yamada | ........... | G01N 35/00871 382/133 |
| 2010/0169811 A1* | 7/2010 | Yamada | ........... | G01N 35/00871 715/764 |
| 2012/0064638 A1* | 3/2012 | Onomichi | .......... | G01N 35/0092 436/501 |
| 2012/0160039 A1* | 6/2012 | Tatsutani | ........... | G01N 35/0092 73/863.91 |
| 2012/0272755 A1* | 11/2012 | Ariyoshi | ................ | G16H 40/63 73/866.3 |
| 2016/0231310 A1* | 8/2016 | Ayyub | ............... | G01N 33/4925 |
| 2016/0320381 A1* | 11/2016 | Holmes | .................. | G01N 35/10 |
| 2017/0297020 A1* | 10/2017 | Lee | ........................... | B01L 7/52 |
| 2019/0049383 A1* | 2/2019 | Kikuchi | ............ | G01N 35/0099 |

FOREIGN PATENT DOCUMENTS

| | | |
|---|---|---|
| WO | 2017/221386 A1 | 12/2017 |
| WO | WO 2018/114295 A1 | 6/2018 |
| WO | 2018/173464 A1 | 9/2018 |

OTHER PUBLICATIONS

Written Opinion of the International Search Authority for International Application No. PCT/EP2021/069142 (six pages).
English translation of Japanese Office Action for International Application No. JP 2023-501386, mailed on Nov. 17, 2023, 7 pages.
European Search Report for European Application No. PCT/EP2021/069142, mailed on Sep. 27, 2021, 2 pages.

* cited by examiner

READY push in & KEEP PUSHING

30

100

1

102

READY in 1 min
Aspirating push in & KEEP PUSHING

30

100

1

102

BLOOD GAS ANALYZER AND SYSTEM COMPRISING A BLOOD GAS ANALYZER, AND USE THEREOF

This application is a national stage filing under 35 U.S.C. § 371 of International Application No. PCT/EP2021/069142, filed on Jul. 9, 2021, which claims priority of European Patent Application No. 20185272.0, filed on Jul. 10, 2020. The contents of these applications are each incorporated herein by reference.

FIELD OF THE INVENTION

The present invention relates to a blood gas analyzer and a system for performing a measurement on analyte parameters in a blood sample, such as a whole blood sample. More specifically, the invention relates to improvements of a user interface of the blood gas analyzer for facilitating users' interaction with the blood gas analyzer with a view to increasing safety and efficiency of use.

BACKGROUND OF THE INVENTION

Blood gas analyzers for measuring physical parameters of analytes in a blood sample by means of analyte sensors are widely used in in the medical and clinical industry. Blood gas analyzers for use with a handheld blood sample container typically comprise an aspiration point for making contact with a forward end of the handheld blood sample container. Once a fluid flow path has been established between the blood sample container and interior flow conduits of the blood gas analyzer, the blood sample or a portion thereof may be aspirated to the analyte sensors.

In the context of point-of-care measurement systems (in the art also referred to as 'bedside' systems) and laboratory environments alike, blood gas analysis is oftentimes undertaken by users, such as nurses, who may not be users specialized in use of blood gas analyzers. In particular, users' correct placement of a handheld blood sample container, such as a syringe or a capillary tube, at an inlet structure of the blood gas analyzer has been found to constitute a challenging aspect in aspiration of the blood sample into the blood gas analyzers. Incorrect positioning or alignment of the blood sample container relative to the inlet structure may not only lead to disturbing delays and/or frustrations in users' daily workflows but may even result in loss of blood samples or contamination of the blood gas analyzer or its surroundings.

So far, these problems have received little attention by developers and owners of blood gas analyzers, and users experiencing such problems have in many instances been left to themselves. In particular, inexperienced so-called 'novice' users of blood gas analyzers have frequently resorted to learning by doing, with all the ensuing implications in terms of hassle, inconvenience and lost efficiency, before they have gradually developed into expert users.

DESCRIPTION OF THE INVENTION

On the above background, it is an object of embodiments of the invention to provide a blood gas analyzer which facilitates users' interaction therewith, notably as far as engagement of a handheld blood sample container with an inlet structure of the blood gas analyzer is concerned. It is a further object of embodiments of the invention to provide a blood gas analyzer, the use of which is convenient to novice as well as expert users.

According to a first aspect, the invention provides a blood gas analyzer for performing a measurement on analyte parameters in a blood sample aspirated into the blood gas analyzer from a handheld blood sample container, the blood gas analyzer comprising a controller and:

a sensor system comprising at least one sensor for detecting a presence, a position and/or an orientation of the handheld blood sample container relative to an inlet structure and for outputting at least one sensor signal indicative of the detected presence, position and/or orientation of the handheld blood sample container;

an aspiration system for aspirating the blood sample from the handheld blood sample container, the aspiration system comprising:

the inlet structure for connecting to the handheld blood sample container;

a user interface system comprising:

an instruction output device for outputting instructions to a user of the blood gas analyzer;

an electronic memory comprising at least two pre-stored sets of user instructions;

wherein the controller is configured to:

receive the at least one sensor signal indicative of the detected presence, position and/or orientation of the handheld blood sample container relative to the inlet structure;

select one of the at least two sets of pre-stored sets of instructions based on an assessment of the at least one sensor signal;

cause the instruction output device to output the selected one of the at least two sets of pre-stored sets of instructions at the instruction output device.

In consequence of the detection of a presence, a position and/or an orientation of the handheld blood sample container relative to an inlet structure, information regarding the handheld blood sample container relative to the inlet structure of the aspiration system is obtained, on the basis of which one of the at least two sets of pre-stored sets of instructions may be selected by the controller and subsequently provided to the user via the instruction output device. Thus, the blood gas analyzer according to the present invention not only provides instructions to the user for the user's handling of the handheld blood sample container and/or of parts of the blood gas analyzer, it also does so in a qualified manner, taking into account the sensor signal, i.e. the presence, position and/or orientation of the blood sample container. Thus, the selected one of the pre-stored sets instructions may match a particular need for assistance, typically reflecting the user's level of experience, a particular challenge or problem encountered, such a misalignment of the handheld blood sample container or lack of complete engagement thereof with an aspiration point of the blood gas analyzer. Furthermore, the estimation regarding the level of assistance or guidance required is performed on the basis of the current behavior of the user, i.e. based on what is happening while the present interaction between the user and the analyzer is taking place, rather than based on information regarding the user during previous interactions. This allows a simple system, since access to historical data is not required. Furthermore, it can be ensured that the offered assistance matches the needs of the user under the given circumstances, such as the actual task being performed, the time of day, etc.

One advantage of the invention is the ability to adapt to the users' real time action and behavior. Adaptive guidance based on users' real time behavior creates value, as the same person's sample handling method may vary or differ depending of the situation and context. For instance, a person's handling may be different or deviate from normal in a stressful and critical situation, where a patient's life is depending of a fast result, compared with a non-critical situation.

Accordingly, instructions are selected by the controller and presented to the user via the instruction output device in dependence of the user's handling of the handheld blood sample container relative to the inlet structure, whereby instructions for, e.g., pushing further or alignment correction of the handheld blood sample container are presented only if the handheld blood sample container needs to be pushed further depression and/or correction of its alignment. Thus, an inexperienced or unfocused user receives adequate guidance, whereas an experienced and/or fully focused user having no need for detailed instructions with regard to a particular aspect of operation is not disturbed in his or her work by unnecessary instructions which are not required under the given circumstances. In that case, the first instruction shown if, for example the sensor system detects that the handheld blood sample container is present, correctly positioned and aligned, may be to keep the handheld blood container in the current position.

Herein, the presence, position and/or orientation of the blood sample container may in particular refer to the presence, position and/or orientation of the blood sample container relative to the inlet structure, such as relative to a mating structure, aspiration point, guide rod, inlet port or the like of the blood gas analyzer.

In the present context the term 'blood gas analyzer' should be interpreted to mean an apparatus capable of performing measurements on analyte parameters in a blood sample aspirated into the blood gas analyzer from a handheld blood sample container. As far as blood gas analysis is concerned, the blood gas analyzer may, e.g., comprise the structure and operate in accordance with the principles disclosed in WO 2017/108646, which is hereby incorporated by reference. The handheld blood sample container may, e.g., comprise a syringe or a capillary tube know per se.

The blood sample may, e.g., be a whole blood sample. In the present context the term 'whole blood sample' should be interpreted to be a sample of blood with all its components, including red and white blood cells, platelets and plasma. The blood may originate from human beings or animals, such as mammals.

The at least one sensor of the sensor system may, e.g., comprise a proximity sensor. Examples of such proximity sensors include, but are not limited to, Hall sensors, ultrasonic sensors, optical sensors, such as photo-diode based sensors, capacitive sensors or inductive sensors. Due to their ability to sense proximity of parts, Hall sensors are particularly suitable for detecting a presence, a position and/or an orientation of the handheld blood sample container in the inlet structure. Furthermore, Hall sensors may be provided as inexpensive standard parts.

Alternatively or additionally, the at least one sensor may comprise a vision-based system, e.g. comprising one or more cameras. In this case, it may be determined, based on an image captured by means of the vision-based system, whether or not a handheld blood sample container at the inlet structure is in a correct position and/or is held with a correct orientation. To this end, the vision-based system may compare the captured image with expected or correct positions and/or orientations. Furthermore, such a vision-based system may be used for determining the kind of blood sample container being present at the inlet structure, e.g. whether the blood sample container is a capillary tube or a syringe.

Alternatively or additionally, the at least one sensor of the sensor system may comprise a sensor which detects presence of blood at the aspiration point. This is an indication that good contact has been established between the handheld blood sample container and the aspiration point, and that the handheld blood sample container is therefore positioned in a correct manner relative to the inlet structure.

Alternatively or additionally, other kinds of sensors may be applied, such as force sensors, mechanical switches, movement sensors, etc.

As experience has shown that insufficient penetration of the handheld blood sample container into the inlet structure, which in some embodiments comprises a cavity surrounding the inlet structure, frequently causes delays or handling errors, the sensor of the sensor system may be configured to determine a position, such as in particular a penetration depth, relative to a stationary part of the blood gas analyzer and/or the inlet structure, of the handheld blood sample container and/or of a displaceable part of the inlet structure configured to make contact with the handheld blood sample container. In case the penetration depth is insufficient, the selected set of pre-stored instructions may be one instructing the user to push the handheld blood sample container further towards the blood gas analyzer.

The instruction output device of the blood gas analyzer may, e.g., include, but is not limited to means known per se, such as a monitor providing instructions via text, images and/or video sequences, a loudspeaker providing audible instructions, such as speech or predetermined sound signals, lamps, such as tell-tale lamps, etc.

The controller's assessment of the at least one sensor signal may, e.g., comprise comparing the received sensor signal to a predefined threshold value, and select one of the pre-stored set of instructions depending on whether the received sensor signal is above or below the predefined threshold value. For instance, in case the blood gas analyzer is handled by an experienced user, the received sensor signal may, e.g., be above the predefined threshold value. In case a novice user is handling the blood gas analyzer, the received sensor signal may, e.g., be below the predefined threshold value. In both cases a corresponding one of the pre-stored set of instructions may be selected, and the instruction output device may accordingly output the selected one of the at least two sets of pre-stored sets of instructions.

In order to adapt the presentation of instructions to the user to different levels of expertise of the user, the at least two pre-stored sets of user instructions may comprise instructions of different level of detail. For example, a first one of the at least two sets of pre-stored sets of instructions may comprise instructions at a first level of detail for the user's interaction with the blood gas analyzer, and a second one of the at least two sets of pre-stored sets of instructions may comprise instructions at a second level of detail for the user's interaction the blood gas analyzer, the first level of detail being greater than the second level of detail.

On the one hand, the first level of detail may, for example, be tailored to match the needs of novice users which are not perfectly acquainted with the aspiration process of the blood gas analyzer. Such users may have a need for more elaborate help with handling the blood gas analyzer and/or its interaction with the handheld blood sample container. Hence, the pre-stored sets of instructions, e.g., comprise detailed instructions on how to achieve adequate connection of the handheld blood sample container to the aspiration system.

On the other hand, the second level of detail may, e.g., be suitable for experienced users which are more acquainted with the aspiration process of the blood gas analyzer and need less elaborate assistance. For instance, the second one of the at least two sets of pre-stored sets of instructions may not comprise further instructions on how to connect the handheld blood sample container to the aspiration system.

The second set of instructions having a relatively low level of detail may conveniently constitute a subset of the first set of instructions, which have a relatively high level of detail.

Memory resources may thus be saved in the sense that the second set of instructions can be stored as part of the first set of instructions, whereby no separate storage space is required for the second set of instructions.

With a view to achieving that the sensor system and the sets of instructions may facilitate the user's positioning of the handheld blood sample container relative to the blood gas analyzer for correct aspiration of blood from the blood sample, the at least one sensor for detecting a position and/or orientation of the handheld blood sample container relative to the inlet structure may be configured to detect a displacement of the receiving structure and/or displacement of the handheld blood sample container relative to an aspiration point of the blood gas analyzer. The aspiration system's aspiration point may be configured to make contact with a forward end of the handheld blood sample container, and the inlet structure may comprise a receiving structure for receiving at least a portion of the handheld blood sample container therein, the receiving structure and aspiration point being arranged to establish a fluid flow path between the forward end of the handheld blood sample container and the aspiration point upon displacement of the receiving structure and/or displacement of the handheld blood sample container relative to the aspiration point.

The assessment of the at least one sensor signal at least may indicate if the forward end of the handheld blood sample container is in fluid communication with the aspiration point, and the at least one of the at least two pre-stored sets of user instructions may comprise a signal instructing the user to push the handheld blood sample container further towards the aspiration point. The at least one of the at least two pre-stored sets of user instructions may additionally or alternatively comprise a signal instructing the user to adjust the angle of the blood sample container relative to the inlet structure. In one embodiment, at least one of the at least two pre-stored sets of user instructions comprises a signal instructing the user to adjust the angle of the blood sample container relative to the inlet structure followed by a signal instructing the user to push the handheld blood sample container. Accordingly, the controller may be configured to select a pre-stored set of instructions based on an assessment of the detected displacement of the handheld blood sample container and/or a displaceable part of the inlet structure relative to a stationary part of the inlet structure, in which case at least one of the at least two pre-stored sets of user instructions may comprise instructions on how to adjust a position and/or orientation of the handheld blood sample container.

For instance, in case the assessment indicates that the forward end of the handheld blood sample container is not in fluid communication with the aspiration point, the controller may, e.g., select a first one of the at least two sets of pre-stored sets of instructions. Accordingly, the first one of the at least two sets of pre-stored sets of instructions may comprise a signal instructing the user to push the handheld blood sample container further towards the aspiration point and/or to adjust the angle of the blood sample container relative to the inlet structure.

In case the assessment indicates that the handheld blood sample container is fully connected with the aspiration point, the controller may, e.g., select the second one of the at least two sets of pre-stored sets of instructions. Accordingly, since the handheld blood sample container is fully connected with the aspiration point, there will typically be no need to instruct the user to push the handheld blood sample container further into the inlet structure, nor to adjust the angle of the blood sample container relative to the inlet structure.

The at least one sensor of the inlet structure may comprise at least two sensors, a first one of which is configured to detect the presence of the handheld blood sample container at a position, in which the forward end of the handheld blood sample container is not in fluid communication with the aspiration point, and a second one of which is configured to detect the presence of the handheld blood sample container at a position, in which the forward end of the handheld blood sample container is in fluid communication with the aspiration point.

For instance, the two sensors may be in the form of two Hall sensors, each detecting a respective position of the handheld blood sample container as described above. As an alternative, the first sensor may be a Hall sensor, whereas the second sensor may be an sensor which detects presence of blood at the aspiration point.

The detected presence of the handheld blood sample container may be used by the controller in selecting an appropriate set of instructions for the user of the blood gas analyzer. For instance, if only the first one of the at least two sensors detects the presence of a handheld blood sample container, this is an indication that the handheld blood sample container is not in fluid communication with the aspiration point. Accordingly, the controller may, e.g., send a signal instructing the user to adjust the angle of the handheld blood sample relative to the blood gas analyzer and/or push the handheld blood sample container further towards the aspiration point, such that the aspiration system may be capable of aspirating blood from the handheld blood sample container.

In case the second one of the at least two sensors detects the presence of a handheld blood sample container, this may indicate that the handheld blood sample container is in fluid communication with the aspiration point. Accordingly, the controller may, e.g., send a signal instructing the user to start the aspiration system or the blood gas analyzer automatically initiate aspiration, such that blood can be aspirated from the handheld blood sample container.

By detecting the presence of the handheld blood sample container using at least two sensors, certainty may thus be obtained that the handheld blood sample container is at a position which enables the aspiration system to aspirate blood from the handheld blood sample container.

The aspiration system may comprise a pump controlled by the controller and operatively connected to the at least one sensor of the inlet structure, and the controller may be configured to activate the pump only upon detection of the handheld blood sample container at a predetermined position and/or orientation thereof relative to the inlet structure. Accordingly, the controller may activate the pump in case the at least one sensor detects the handheld blood sample container at a specified position and/or orientation relative to the inlet structure. Thereby, it may be ensured that the pump is activated when the handheld blood sample container is at a position where it is possible to aspirate blood from the handheld blood sample container. This may reduce the number of lost samples, and thereby increase the number of successful handheld measurements. Further, the risk of the occurrence of cavitation in the internal liquid conduits of the blood gas analyzer may be reduced or eliminated.

In order to adopt the selection of instructions to a specific characteristic of the handheld blood sample container, such as its type, e.g. syringe, capillary tube or vacutainer tube, the inlet structure may comprise an interface allowing a user to manually input a characteristic of the handheld blood sample container, such as its type, e.g. syringe, capillary tube or vacutainer tube, such as a touchscreen button, e.g. as part of the instruction output device, or a mechanical push button.

In order to adopt the selection of instructions to a specific characteristic of the handheld blood sample container, such as its type, e.g. syringe, capillary tube or vacutainer tube, the inlet structure may comprise an interface for automatically determining at least one characteristic of the handheld blood sample container. Suitable identifiers of the handheld blood sample container may include one or more of at least one radio frequency (RF) tag, BlueTooth emitter, other types of wireless devices, a protrusion or depression in an outer surface of the handheld blood sample container, or any other mechanically detectable portion thereof, a specific outer dimension of the handheld blood sample container or a portion thereof, or a machine readable code, such as a quick reader (QR) code or a barcode. The interface for automatically determining at least one characteristic of the handheld blood sample container may comprise any suitable receiver or sensor for determining any one of the aforementioned characteristics.

The instruction output device may comprise a monitor, and the pre-stored sets of instructions may comprise animated video sequences. In the present context, the term 'animated video sequences' should be interpreted to mean a sequence in which visual elements are manipulated to appear as moving images. Animations may be made with computer-generated imaginary. The illusionary effect of animation may be achieved by a rapid succession of sequential images that minimally differ from each other. For instance, the animated video sequences may show a suggested adjustment of the handheld blood sample container from the user's point of view. Further, animated video sequences may be generated to enhance the user's perception of any specific action and/or a haptic feedback to the user associated with any such action, and to illustrate the envisaged action from various perspectives. The animated video sequences may be generated to resemble to actual situation to which the user is presented, i.e. look like the task at hand.

In addition to comprising the inlet structure which receives handheld blood sample containers, the blood gas analyzer may be adapted to handle blood sample containers, which are not handheld, but which are instead handled in an automatic manner. For instance, the analyzer may comprise a sampler bed comprising one or more slots, each slot being configured to receive a sampler containing a blood sample. In the case that the sampler bed comprises two or more slots, the analyzer may further be adapted to perform simultaneous handling of two or more samples, including handling a queue of samples and keeping track of which information relates to which samples. The samples may not be handled in the same manner at a given point in time. For instance, one sample may be analyzed while one or more other samples are in queue to be analyzed.

According to a second aspect, the invention provides a system for performing a measurement on analyte parameters in a blood sample, comprising a blood gas analyzer and a handheld blood sample container; the blood gas analyzer comprising:
  a controller;
  a sensor system comprising at least one sensor for detecting a presence, a position and/or an orientation of the handheld blood sample container relative to an inlet structure and outputting at least one sensor signal indicative of the detected presence, position and/or orientation of the handheld blood sample container;
  an aspiration system for aspirating the blood sample from the handheld blood sample container, the aspiration system comprising:
    the inlet structure for connecting to the handheld blood sample container;
  a user interface system comprising:
    an instruction output device for outputting instructions to a user of the blood gas analyzer;
    an electronic memory comprising at least two pre-stored sets of instructions;
wherein the controller of the blood gas analyzer is configured to:
  receive the at least one sensor signal indicative of the detected presence, position and/or orientation of the handheld blood sample container in the inlet structure;
  select one of the at least two sets of pre-stored sets of instructions based on an assessment of the at least one sensor signal;
  cause the instruction output device to output the selected one of the at least two sets of pre-stored sets of instructions at the instruction output device.

The blood gas analyzer may in particular include the blood gas analyzer according to the first aspect of the invention, including any embodiment thereof disclosed herein. Accordingly, the remarks set forth above with reference to the first aspect of the invention are equally applicable in relation to the system of the second aspect of the invention.

The inlet structure may comprise an interface for automatically determining at least one characteristic of the handheld blood sample container. Accordingly, the handheld blood sample container may comprise an identifier identifying its at least one characteristic, and the blood gas analyzer may comprise a data capturing device for deriving the at least one characteristic from the identifier of the blood sample container. According to this embodiment, each handheld blood sample container characteristic is preferably determined by an identifier unique to that characteristic. Suitable identifiers of the handheld blood sample container may include one or more of at least one radio frequency (RF) tag, BlueTooth emitter, other types of wireless devices, a protrusion or depression in an outer surface of the handheld blood sample container, or any other mechanically detectable portion thereof, a specific outer dimension of the handheld blood sample container or a portion thereof, or a machine readable code, such as a quick reader (QR) code or a barcode. The interface for automatically determining at least one characteristic of the handheld blood sample container may comprise any suitable receiver or sensor for determining any one of the aforementioned characteristics.

The handheld blood sample container may, e.g., comprise a syringe, a capillary tube or a vacutainer. The aforementioned characteristic of the handheld blood sample container may, e.g., include any characteristic of its type, such as, for example, a numerical identifier recognizable by the controller, or a dimension or volume thereof.

The invention further provides a use of a system according to the second aspect of the invention for point-of-care (POC) measurement on analyte parameters in a blood sample. POC measurement is also referred to as 'bed site' measurement in the art. In the present context, the term 'point-of-care measurement' should be understood to mean measurements which are carried out in close proximity to a patient, i.e. measurements that are not carried out in a laboratory. Thus, according to this embodiment, the user of the blood gas analyzer performs measurement of a blood sample in a handheld blood sample container in the proximity of the patient, from whom the blood sample is taken, e.g. in the hospital room or ward accommodating the patient's bed, or in a nearby room of the same hospital department. In such use, the level of expertise of the user oftentimes varies from novice to experienced, and the capability of the blood gas analyzer to automatically output instructions matching each individual user's skills on the basis of sensor input is thus particularly beneficial in such environments.

BRIEF DESCRIPTION OF THE DRAWINGS

The invention will now be described in further details with reference to the accompanying drawings, in which.

DETAILED DESCRIPTION OF THE DRAWINGS

Figure 1:
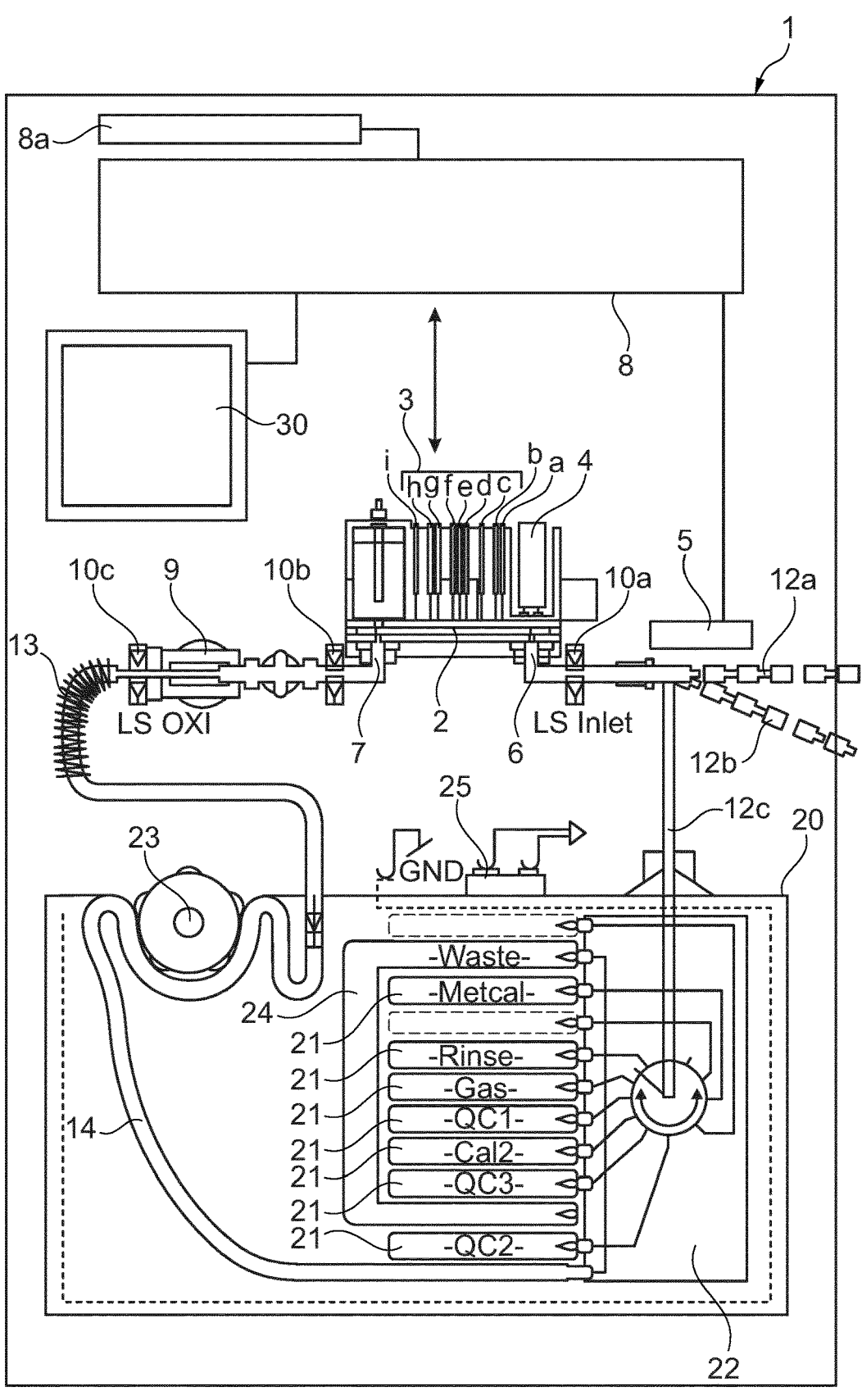
FIG. 1 is a schematic diagram of a blood gas analyzer according to an embodiment of the invention.

FIG. 1 is a schematic diagram of a blood gas analyzer 1 having a controller 8, one or more analyte sensors 3(*a-i*) and 4, a measurement chamber 2, and fluid handling infrastructure 20. For performing measurements, the user may provide a blood sample at an inlet structure 12 *a/b* of the blood gas analyzer 1 using a handheld blood sample container 100 (see FIGS. 3-10). When connecting the handheld blood sample container to the inlet structure 12*a/b*, a sensor system 5 detects a presence, a position and/or an orientation of the handheld blood sample container. A sensor signal of the detected presence, position and/or orientation of the handheld blood sample is provided from the sensor system 5 to the controller 8. The controller 8 assesses whether the detected sensor signal indicates if the handheld blood sample container 100 is in fluid communication with an aspiration point.

In case the assessment indicates that the handheld blood sample container 100 is not fully connected with the aspiration point, the controller 8 may, e.g., select a first one of at least two sets of pre-stored sets of instructions stored in an electronic memory 8*a* and output the selected pre-stored set of instructions at an output device, such as a monitor 30. The first one of the at least two sets of pre-stored sets of instructions may comprise a signal instructing a user to push the handheld blood sample container further towards the aspiration point, thereby providing further help to the user on how to handle the blood gas analyzer 1 and the handheld blood sample container 100. The first one of the at least two sets of pre-stored sets of instructions may, e.g., be tailored to match the needs of novice users that are not perfectly acquainted with handling of the blood gas analyzer 1.

If or once the controller's assessment of the sensor signal provided by sensor system 5 indicates that the handheld blood sample container is fully connected with the aspiration point, the controller 8 may, e.g., select a second one of the at least two sets of pre-stored sets of instructions. Accordingly, once the handheld blood sample container is fully connected with the aspiration point, there may be no need to instruct the user to push the handheld blood sample container further into the inlet structure 12*a/b*. The output of the first set of instructions may hence be omitted.

The sensor 5 may comprise at least two sensors, a first one of which may detect a presence, a position and/or an orientation of the handheld blood sample container 100 of the handheld blood sample container at a position, in which the handheld blood sample container 100 is not in fluid communication with the aspiration point. The second sensor may detect a presence, a position and/or an orientation of the handheld blood sample container of the handheld blood sample container at a position, in which the handheld blood sample container is in fluid communication with the aspiration point. Accordingly, the first or the second sensor may send a sensor signal to the controller 8 depending on the detected position of the handheld blood sample container 100.

The blood sample is transferred from the aspiration point through an inlet 6 to the measurement chamber 2 comprising a plurality of analyte sensors 3 and 4. The analyte sensors 3 and 4 are arranged to provide measurements on analyte parameters in the blood sample. The analyte sensors 3 and 4 generate signals that are representative of a physical parameter for the respective analyte and provide the signals to the controller 8. The controller 8 is adapted to receive and process signals from the analyte sensors 3 and 4 and present the processed signals as output to the user at the monitor 30. The fluid handling infrastructure 20 includes a number of reservoirs 21 pre-filled with process liquids for, e.g., rinsing/wash-out, calibration and quality control tasks, as indicated in FIG. 1. The exact composition of a given process liquid may be stored in a chip 25. The process liquid for a given process step may be selected by a fluid selector valve 22, and via feed line 12*c* transferred through the aspiration point to the measurement chamber 2. Correct filling of the measurement chamber 2 is monitored by means of liquid sensors 10(*a-c*), located, e.g., at the aspiration point, at an outlet of the measurement chamber 2, and after a measurement device 9. The fluid flow through the blood gas analyzer 1 is driven by a pump 23, connected to a measurement device 9 via a fluid line 13. The discharged process fluids are transported through fluid line 14 to a waste reservoir 24.

Figure 2:
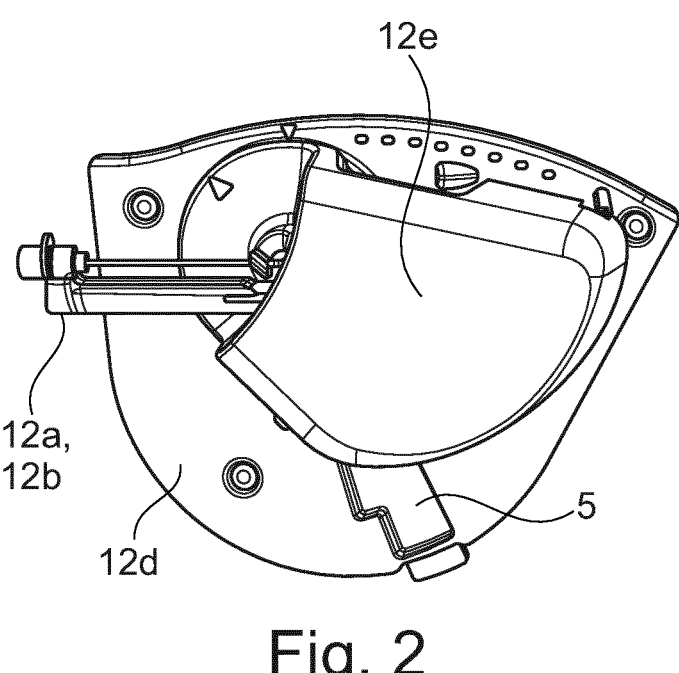
FIG. 2 is a side-view of a blood gas analyzer according to an embodiment of the invention.
Figure 3:
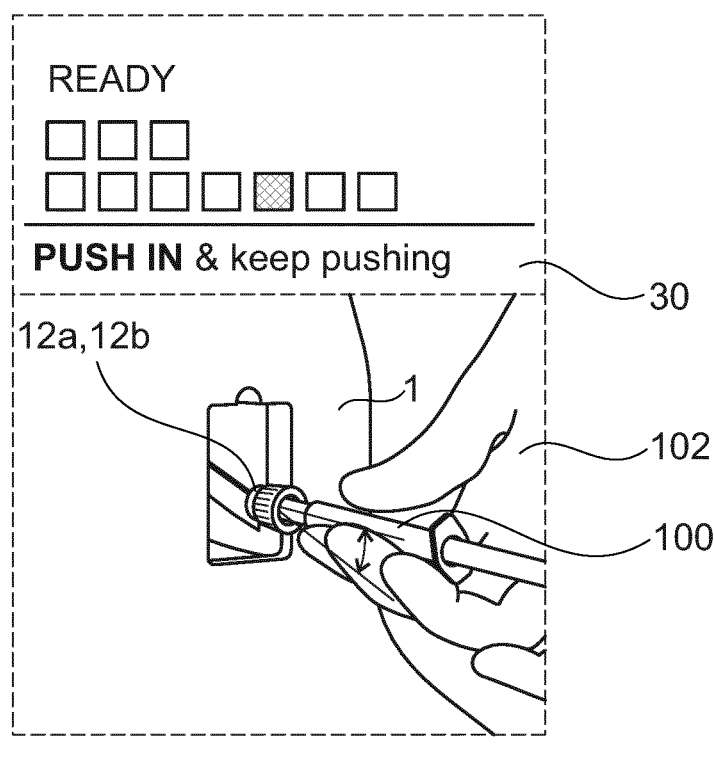
FIGS. 3-10 illustrate visual instructions presented through a blood gas analyzer according to an embodiment of the invention.

FIG. 2 is a side-view of a blood gas analyzer inlet structure. The blood gas analyzer of FIG. 2 may be in accordance with the blood gas analyzer according to the FIG. 1. Accordingly, the remarks set forth above with reference to FIG. 1 are equally applicable here. The blood gas analyzer further has a stationary part 12*d* and a displaceable part 12*e*. The sensor 5 of the blood gas analyzer may be configured to detect a position, such as in particular a penetration depth, relative to the stationary part 12*d* of the blood gas analyzer and/or the inlet structure 12*a/b*, of the handheld blood sample container 100 and/or of the displaceable part 12*e* of the inlet structure 12*a/b* configured to make contact with the handheld blood sample container. In the case that the detected penetration depth is insufficient, the blood gas analyzer may select a set of pre-stored instructions, instructing a user to push the handheld blood sample container further towards the blood gas analyzer, thereby ensuring that the handheld blood sample container is inserted properly into the inlet structure 12a/b.

Figure 4:
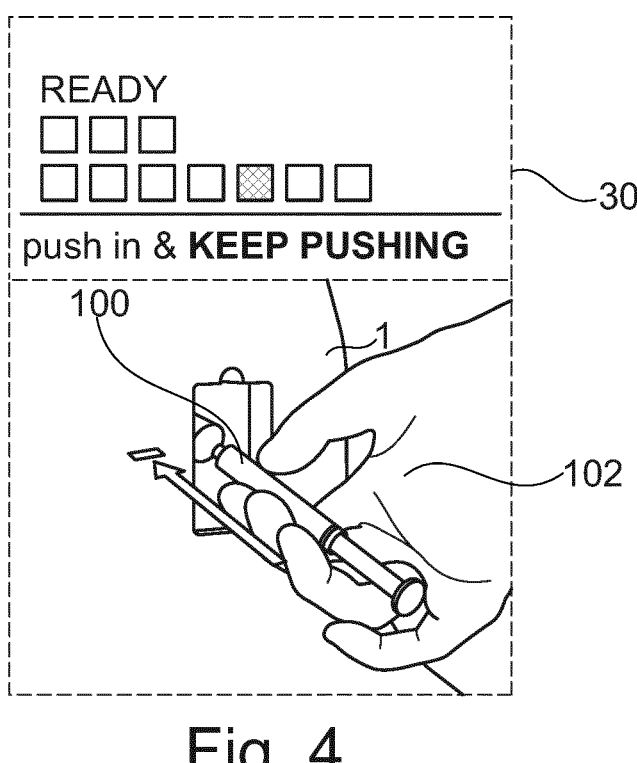
Figure 5:
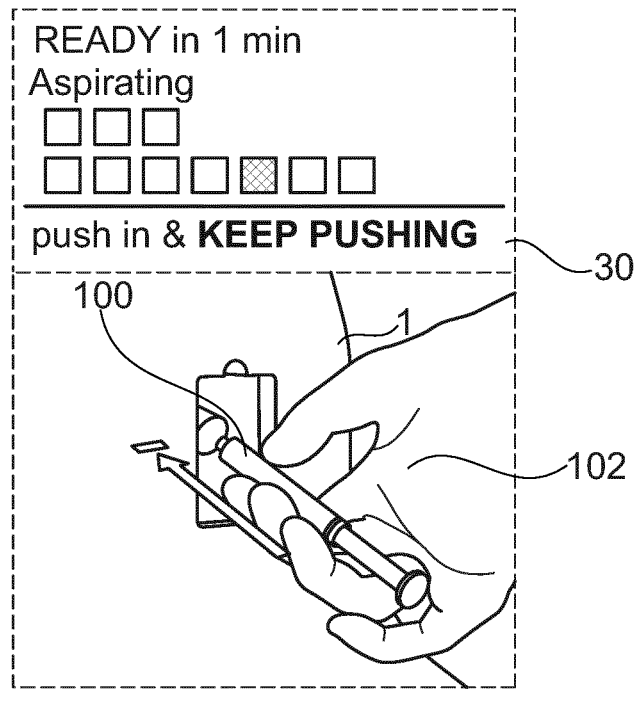
Figure 6:
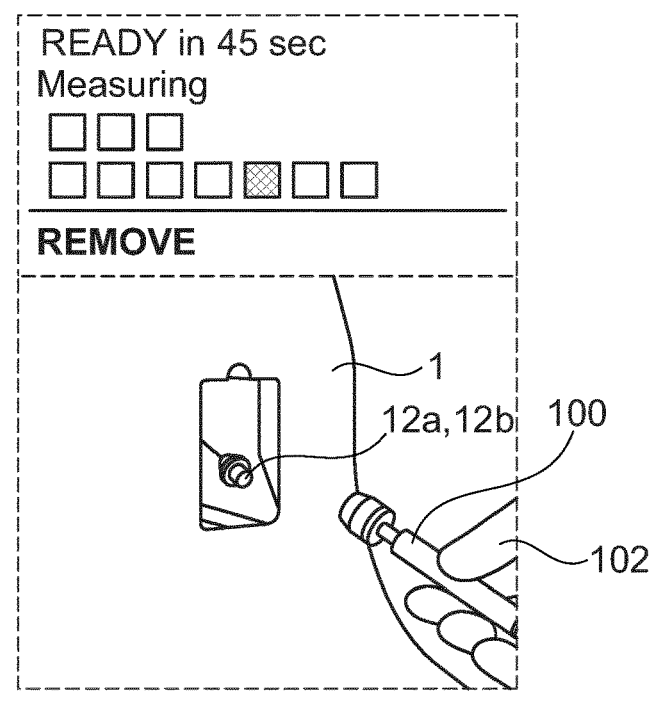

FIGS. 3-10 illustrate examples of instructions presented through a blood gas analyzer. A user 102 connects a handheld blood sample container 100 to an inlet structure 12a/b of the blood gas analyzer 1. Such a handheld blood sample container 100 may, e.g., comprise a syringe or a capillary tube. A sensor system 5 (see FIGS. 1 and 2) of the blood gas analyzer may detect a presence, a position and/or an orientation of the handheld blood sample container 100 and select a pre-stored set of instructions in a manner described above with reference to FIG. 1. In the embodiment of FIGS. 3-10, the instruction shown at the monitor 30 instructs the user 102 to push the handheld blood sample container 100 into the inlet structure 12a/b of the blood gas analyzer 1. In FIG. 4 the user 102 is instructed to adjust the angular orientation of the handheld blood sample container 100, while the blood gas analyzer 1 instructs the user 102 to push the handheld blood sample container 100 into the inlet structure 12a/b of the blood gas analyzer 1. In FIGS. 5 and 6 the blood gas analyzer instructs the user 102 to keep pushing the handheld blood sample container 100 into the inlet structure 12a/b of the blood gas analyzer 1 while blood is being aspirated.

Figure 7:
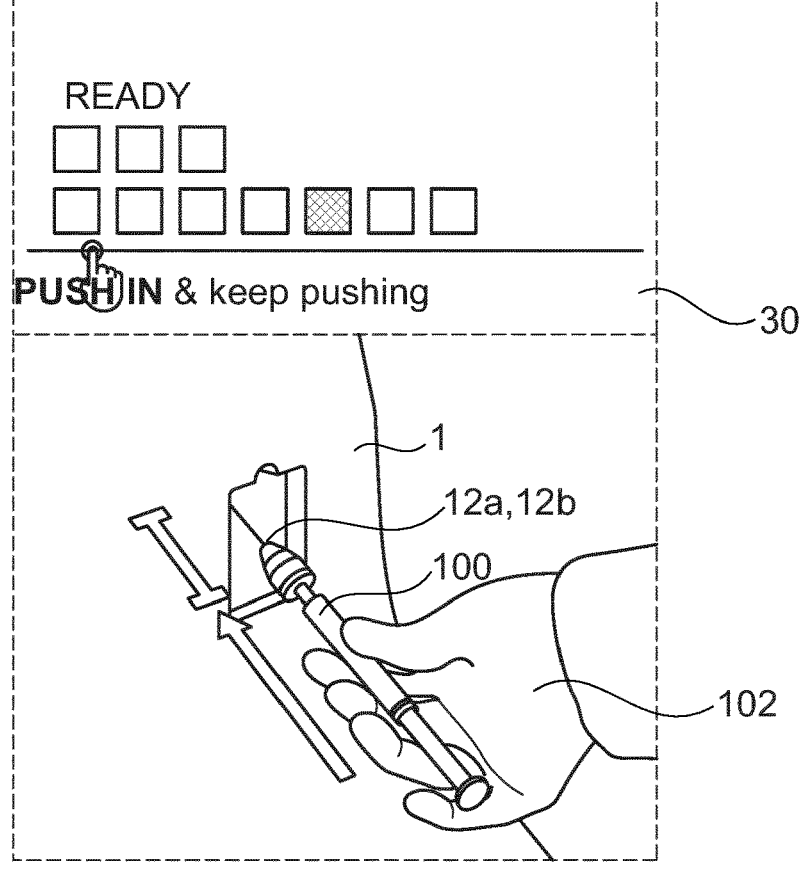
Figure 8:
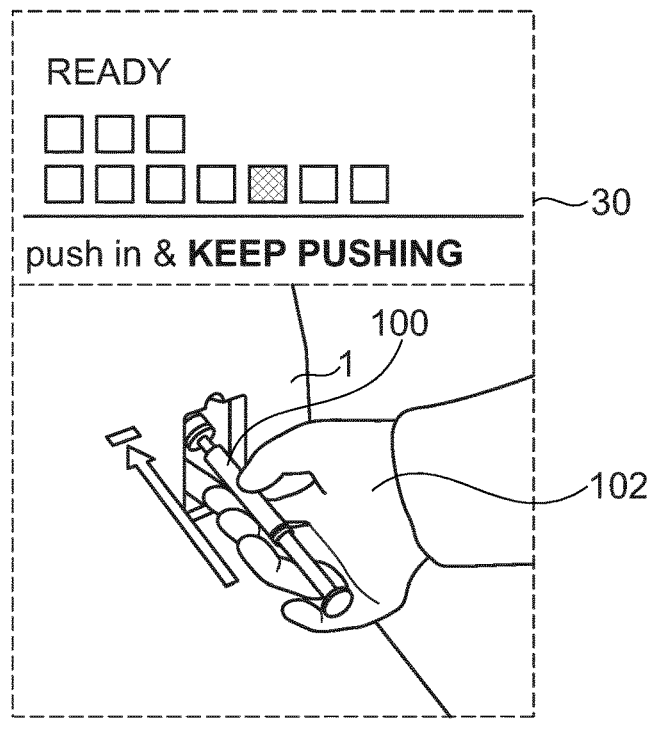
Figure 9:
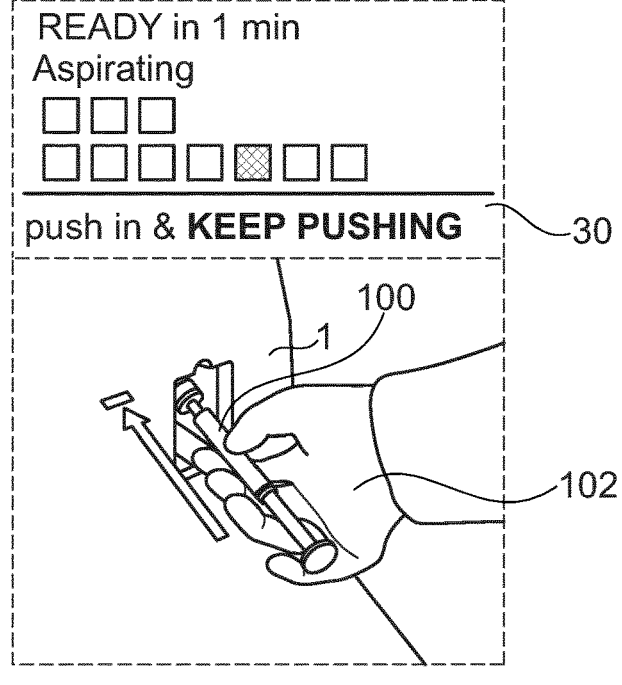
Figure 10:
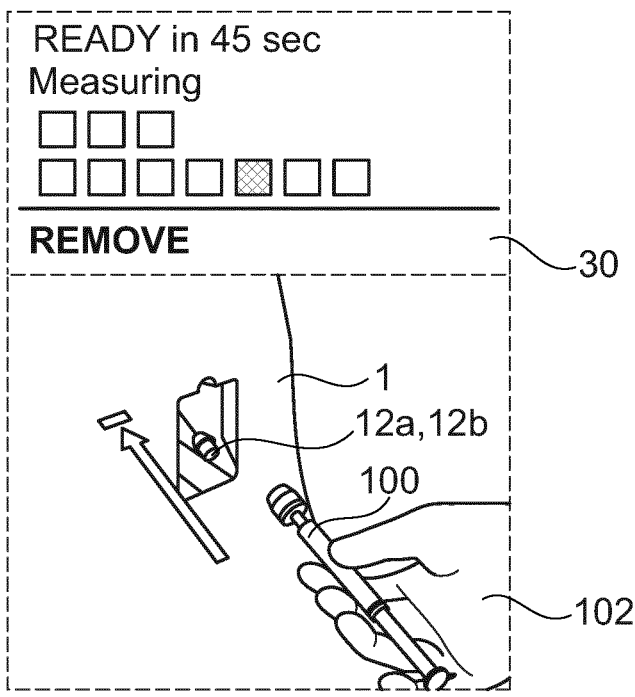

When the sensor system 5 detects a position of the handheld blood sample container 100, the blood gas analyzer 1 starts aspirating the blood sample from the handheld blood sample container 100, as illustrated in FIGS. 7 and 8. When the aspiration is completed, the blood gas analyzer 1 instructs the user 102 to remove the handheld blood sample container 100 from the blood gas analyzer 1, as illustrated in FIG. 9, and starts measuring of the blood sample, cf. FIG. 10.

The instructions as illustrated in FIGS. 3-7 are selected by the controller in case the sensor system 5 indicates that the user may have difficulties in advancing the handheld blood sample container 100 to a sufficient penetration depth for its forward end to reach the aspiration point within the blood gas analyzer. If, however, the sensor system 5 indicates that the user readily advances the handheld blood sample container 100 to a position, in which fluid flow communication is established with the internal flow conduits of the blood gas analyzer, only the instructions illustrated in FIGS. 7-10 are selected. It will thus be appreciated that the set of instructions illustrated in all of FIGS. 3-7 taken together illustrates a first set of instructions having a first, relatively high level of detail tailored to match the skills and experience of an inexperienced, novice user. The subset of instructions illustrated in FIGS. 7-10, not including the subset of instructions of FIGS. 3-6, illustrates a second set of instructions having a second, relatively low level of detail matching the skills and experience of an experienced user.

In case the instructions include video instructions, such as animated video instructions, the subset of video instructions having the first, relatively high level of detail may be longer, i.e. include more details, more frames and/or played at slowed pace than the subset of video instructions having the second, relatively low level of detail.

The invention claimed is:

1. A blood gas analyzer for performing a measurement on a blood sample aspirated into the blood gas analyzer from a handheld blood sample container, the blood gas analyzer comprising:
   (a) a controller;
   (b) a sensor system comprising at least one sensor that is structurally configured and positioned to enable the at least one sensor to perform the following:

(1) detecting a presence, a position, and/or an orientation of the handheld blood sample container relative to an inlet structure, and
(2) outputting at least one sensor signal indicative of the detected presence, position, and/or orientation of the handheld blood sample container; and
(c) an aspiration system that is structurally configured and positioned to enable the aspiration system to aspirate the blood sample from the handheld blood sample container, the aspiration system comprising:
   (1) the inlet structure that is structurally configured and positioned to enable the inlet structure to connect to the handheld blood sample container; and
   (2) a user interface system comprising:
      (A) an instruction output device that is structurally configured and positioned to enable the instruction output device to output instructions to a user of the blood gas analyzer; and
      (B) an electronic memory comprising at least two pre-stored sets of user instructions;
   wherein the controller is connected to each of the sensor system and the aspiration system such that the controller is structurally configured and positioned to enable the controller to:
      receive the at least one sensor signal indicative of the detected presence, position and/or orientation of the handheld blood sample container relative to the inlet structure;
      select one of the at least two pre-stored sets of instructions based on an assessment of the at least one sensor signal performed by the controller; and
      cause the instruction output device to output to the user at least a portion of the selected one of the at least two pre-stored sets of instructions at the instruction output device.

2. The blood gas analyzer according to claim 1, wherein a first one of the at least two pre-stored sets of instructions comprises instructions at a first level of detail for a user's interaction with the blood gas analyzer, and wherein a second one of the at least two pre-stored sets of instructions comprises instructions at a second level of detail for the user's interaction the blood gas analyzer, the first level of detail being greater than the second level of detail.

3. The blood gas analyzer according to claim 2, wherein the first one of the at least two pre-stored sets of instructions further comprises user instructions for the user to adjust the position and/or orientation of the handheld blood sample container relative to the inlet structure.

4. The blood gas analyzer according to claim 1, wherein
   the at least one sensor for detecting a presence, position and/or orientation of the handheld blood sample container relative to the inlet structure is configured to detect a displacement of the handheld blood sample container relative to the inlet structure.

5. The blood gas analyzer according to claim 4, wherein the assessment of the at least one sensor signal at least indicates if the handheld blood sample container is in fluid communication with the inlet structure, and wherein at least one of the at least two pre-stored sets of user instructions comprises a signal instructing the user to push the handheld blood sample container further towards the point inlet structure, wherein the instruction output device is configured to output the signal to the user.

6. The blood gas analyzer according to claim 1, wherein the at least one sensor of the inlet structure comprises at least two sensors, wherein a first one of the at least two sensors is configured to detect the presence of the handheld blood sample container at a position, in which the handheld blood sample container is not in fluid communication with the aspiration point, and wherein a second one of the at least two sensors is configured to detect the presence of the handheld blood sample container at a position, in which the handheld blood sample container is in fluid communication with the aspiration point.

7. The blood gas analyzer according to claim 1, wherein the at least one sensor for detecting the presence, position, and/or orientation of the handheld blood sample container relative to the inlet structure comprises a hall sensor.

8. The blood gas analyzer according to claim 1, wherein the aspiration system comprises a pump operably connected to the controller and operatively connected to the at least one sensor of the inlet structure, and wherein the controller is configured to activate the pump only upon detection of the handheld blood sample container at a predetermined position and/or orientation thereof relative to the inlet structure.

9. The blood gas analyzer according to claim 1, wherein the inlet structure comprises an interface to automatically determine at least one characteristic of the handheld blood sample container.

10. The blood gas analyzer according to claim 1, wherein the instruction output device comprises a monitor, and wherein the pre-stored sets of instructions comprise animated video sequences of instructions to the user.

11. A system for performing a measurement on analyte a blood sample, comprising a blood gas analyzer and a handheld blood sample container; the blood gas analyzer comprising:

(a) a controller;

(b) a sensor system comprising at least one sensor that is structurally configured and positioned to enable the at least one sensor to perform the following:
    (1) detecting a presence, a position, and/or an orientation of the handheld blood sample container relative to an inlet structure, and
    (2) outputting at least one sensor signal indicative of the detected presence, position and/or orientation of the handheld blood sample container; and (c) an aspiration system that is structurally configured and positioned to enable the aspiration system to aspirate the blood sample from the handheld blood sample container, the aspiration system comprising:
    (1) the inlet structure that is structurally configured and positioned to enable the inlet structure to connect to the handheld blood sample container; and (2) a user interface system comprising:
    (A) an instruction output device that is structurally configured and positioned to enable the instruction output device to output user instructions to a user of the blood gas analyzer; and
    (B) an electronic memory comprising at least two pre-stored sets of machine readable instructions;
wherein the controller of the blood gas analyzer is connected to each of the sensor system and the aspiration system such that the controller is structurally configured and positioned to enable the controller of the blood gas analyzer is configured to:
    receive the at least one sensor signal indicative of the detected presence, position and/or orientation of the handheld blood sample container relative to the inlet structure;
    select one of the at least two pre-stored sets of machine readable instructions based on an assessment of the at least one sensor signal performed by the controller; and
    cause the instruction output device to output to the user at least a portion of the selected one of the at least two pre-stored sets of machine readable instructions at the instruction output device.

12. The system according to claim 11, wherein the inlet structure comprises an interface to automatically determine at least one characteristic of the handheld blood sample container.

13. The system according to claim 12, wherein the handheld blood sample container comprises identifying at least one characteristic, and wherein the blood gas analyzer comprises a data capturing device for deriving the at least one characteristic of the handheld blood sample container, wherein the data capturing device is in communication with the controller.

14. The system according to claim 11, wherein the handheld blood sample container comprises at least one of a syringe and a capillary tube.

15. A method of performing point-of-care (POC) measurement of at least one analyte in a blood sample, the method comprising:
    providing the system for performing a measurement on the blood sample of claim 11;
    obtaining the blood sample from a patient;
    aspirating blood from the blood sample into the blood gas analyzer of said system for performing a measurement of the at least one analyte; and
    measuring the at least one analyte in said blood.

* * * * *